United States Patent [19]

Haeger et al.

[11] Patent Number: 5,059,619

[45] Date of Patent: Oct. 22, 1991

[54] STABLE FREEZE-DRIED POLYHEMATOPORPHYRIN ETHER/ESTER

[75] Inventors: Bruce E. Haeger, Highland Mills; James R. Lawter, Goshen; Vijay H. Naringrekar, Suffern; Michael C. Cucolo, Yonker, all of N.Y.

[73] Assignee: Quadra Logic Technologies, Inc., Vancouver, Canada

[21] Appl. No.: 366,374

[22] Filed: Jun. 14, 1989

[51] Int. Cl.$^5$ .............................................. A61K 31/40
[52] U.S. Cl. .................................... 514/410; 540/145
[58] Field of Search ........................ 540/145; 514/410

[56] References Cited

U.S. PATENT DOCUMENTS

| | | | |
|---|---|---|---|
| 2,858,320 | 10/1958 | Woods | 260/314 |
| 4,649,151 | 3/1987 | Dougherty et al. | 514/410 |
| 4,753,958 | 6/1988 | Weinstein et al. | 514/410 |
| 4,882,234 | 11/1989 | Lai et al. | 514/185 |

FOREIGN PATENT DOCUMENTS 0210351 2/1987 European Pat. Off. .
WO90/00392 1/1990 PCT Int'l Appl. .

OTHER PUBLICATIONS

Remington's Pharmaceutical Sciences, 15th Ed. (1975), pp. 1483–1485.
Lachman et al., The Theory and Practice of Industrial Pharmacy, 2nd Ed. (1976), pp. 521–524, 599, 600, 618 & 619.

Primary Examiner—Richard L. Raymond
Attorney, Agent, or Firm—Kenneth J. Dow

[57] ABSTRACT

A pharmaceutical composition comprising a freeze-dried preparation of polyhematoporphyrin ether/esters wherein said freeze dried preparation does not contain sodium chloride. Upon reconstitution, the pharmaceutical composition is a photosensitizer preparation useful in photodynamic therapy.

6 Claims, No Drawings

STABLE FREEZE-DRIED POLYHEMATOPORPHYRIN ETHER/ESTER

The invention relates to freeze-dried compositions containing tumor-selective porphyrin compounds useful in photodynamic therapy. More particularly, the invention relates to freeze-dried compositions containing a polyhematoporphyrin ether/ester preparation known as PHOTOFRIN II ® and processes for producing the freeze-dried preparation.

BACKGROUND OF THE INVENTION

Photodynamic therapy using porphyrins and related compounds has been known in the art for some time. As early as the 1940's, it was known that porphyrin had the capability of fluorescing in tumor tissue. The porphyrins appear to localize in tumor tissue where they absorb light at certain wavelengths when irradiated, providing a means to detect the tumor by the location of the fluorescence. Accordingly, preparations containing the porphyrins are useful in the diagnosis and detection of such tumor tissues. In addition, the porphyrin compounds also have the capability of destroying the tumor tissue when irradiated at the appropriate wavelength, possibly through the formation of singlet oxygen. (Weishaupt, K. R., et al., *Cancer Research* (1976) pp. 2326-2329).

The use of these light absorbing compounds, particularly those related to porphyrins, has been well established as a treatment for tumors when administered systemically. The utility of the compounds rests upon their ability to localize in neoplastic tissue while being cleared from the normal surrounding tissue. (See, for example, Dougherty, T. J. et al., "Cancer: Principles and Practice of Oncology" (1982). V. T. de Vita, Jr. et al., eds., pp. 1836-1844).

In addition to systemic use for the treatment of tumors, more recent publications have specified alternative uses for the porphyrin compounds. For example, the use of porphyrins in the treatment of skin diseases has been described in U.S. Pat. No. 4,753,958. The use of photosensitizing compounds to sterilize biological samples containing infectious organisms such as bacteria and virus has been disclosed in U.S. Pat. No. 4,727,027 where the photosensitizer is furocumarin and its derivatives. Photosensitizing porphyrins are useful in the detection and treatment of atherosclerotic plaques, as described in U.S. Pat. Nos. 4,512,762 and 4,574,682. In addition, U.S. Pat. Nos. 4,500,507 and 4,485,806 describe the use of radiolabeled porphyrin compounds for tumor imaging.

A photosensitizer preparation widely used in the early stages of photodynamic therapy both for detection and treatment was a crude derivative of hematoporphyrin, also called hematoporphyrin derivative, HpD, or Lipson derivative, prepared as described by Lipson et al., in J. Natl. Cancer Inst. (1961) 26: 1-8. Considerable work has been done using this preparation and the use of this derivative in treatment of malignancy has been widely reported. (Cancer Res. (1978) 38:2628-2635; J. Natl. Cancer Inst. (1979) 62:231-237).

Dougherty and coworkers prepared a more effective form of the hematoporphyrin derivative which is prepared by ultrafiltration of HpD to reduce the content of low molecular weight species. This work is the subject of U.S. Pat. No. 4,649,151, hereby incorporated by reference into the present application, which further describes in detail methods for phototherapeutic treatment of a patient using the compositions described therein. This form of the drug is actually a complex mixture containing porphyrin units joined by ether linkages (Dougherty, T. J. et al., Adv. Exp. Med. Biol. (1983) 160:3-13) and ester linkages (Kessel, D. et al., *Photochem. Photobiol.* (1987) 36:463-568). This complex mixture, referred to herein as polyhematoporphyrin ethers/esters ("PHE"), has been available under the trademark PHOTOFRIN II ®, and is the subject of the present invention.

At present, PHE has been supplied as a 2.5 mg/ml or 5 mg/ml solution containing PHE in normal saline. The PHE degrades rapidly when exposed to heat and is therefore relatively unstable at room temperature. Accordingly, the solution must be kept frozen to maintain its potency. In addition, the solution tends to show significant particulate formation at higher temperatures which makes it undesirable for use as an injectable product unless it is kept frozen and thawed immediately prior to use.

The use of such a frozen solution has many disadvantages, however. Because it has to be kept frozen, it must be shipped and stored in a frozen state, necessitating the use of special refrigeration conditions. For example, the product must be shipped in special containers using dry ice or the like as a refrigerant. This is a major drawback, adding to the cost and logistics of using the product. At the point of use, the frozen solution must be stored at −20° C., which is below the operating temperatures of some freezers thereby necessitating special freezer equipment. In addition, the frozen product must undergo a thawing period and is therefore not useable immediately with a patient.

Thus, there is a need for a formulation of PHE which is stable at room temperature for extended periods of time, does not have to be kept frozen and therefore does not require special shipping and storage conditions.

It is known in the art that freeze-drying a product which is relatively unstable in aqueous solution can result in a product that is stabilized and therefore has a longer shelf life than an aqueous solution. Additionally, a freeze-dried product has an advantage over a product in powder form in that it is rapidly soluble and easily reconstituted prior to administration by injection. Another advantage of freeze-drying a product unstable in aqueous solution is that it can be processed and filled into dosage containers in a liquid state, dried at low temperatures thereby eliminating adverse thermal effects, and stored in the dry state where it may be more stable. (See Remington's Pharmaceutical Sciences, 15th edition., pp. 1483-1485 (1975)). Thus, freeze-drying would be an ideal method of obtaining a formulation of PHE which would have the desired stability at room temperature and therefore would not have to be stored frozen.

Weinstein et al., in U.S. Pat. No. 4,753,958 discloses a topical formulation of hematoporphyrin derivative for the treatment of psoriasis and other cutaneous diseases which is prepared by freeze-drying a 5 mg/ml saline solution of PHE and reconstituting it in an appropriate topical vehicle.

Although freeze-drying the frozen PHE saline solution may be useful for the purpose of preparing a product suitable for topical application, the present inventors have found that certain problems are encountered when freeze-drying the saline solution which make formulation difficult and the resulting product unacceptable for administration by injection. When attempts were made to freeze-dry a concentrated saline solution containing 15 mg/ml PHE and 5.4% sodium chloride (the amount of sodium chloride necessary to yield an isotonic solution after reconstitution with Water For Injection for a 2.5 mg/ml PHE solution), partial precipitation (salting out) of the PHE active ingredient occurred. In addition, as a consequence of the precipitation, filtration of the concentrate is extremely difficult, requiring frequent filter changes. Also, some of the active ingredient is removed on the filters. Further, the freeze-dried product is not homogeneous and consists of separate sodium chloride and PHE phases. Separation of the phases probably takes place during freezing due to differential crystallization.

Alternatively, a saline solution containing 2.5 mg/ml PHE could be freeze-dried, but the freeze-drying process would be very long, since more water would have to be removed. In addition, the same problems with filtration and precipitation would be encountered due to the presence of sodium chloride in the solution.

There is a clear need, therefore, to provide a formulation of PHE which is stable at room temperature over an extended period of time and therefore does not require freezing, but which overcomes the problems associated with freeze-drying the aqueous saline solution.

SUMMARY OF THE INVENTION

It is an object of the present invention to provide a method of formulating PHE which is relatively unstable in aqueous solution so that a product is produced which is stable at room temperature for extended periods of time.

It is also an object of the present invention to provide a PHE preparation which is homogeneous and suitable for administration by injection.

Yet another object of the present invention is to provide a method of freeze-drying a PHE solution which avoids the problems associated with freeze-drying a PHE saline solution.

These and other objects and advantages of the present invention will be readily apparent to those of skill in the art from the following embodiments.

The present invention resides in the discovery that a PHE photosensitizer composition which is stable at room temperature over extended periods of time can be obtained by freeze-drying. It is further based on the discovery that the problems associated with freeze-drying a PHE saline solution can be avoided by eliminating the sodium chloride from the solution and freeze-drying the PHE from an aqueous solution, then reconstituting with a non-saline diluent such as 5% Dextrose Injection.

DETAILED DESCRIPTION

It has been surprisingly discovered that a polyhematoporphyrin ether/ester preparation which is stable at room temperature for extended periods of time can be formulated by freeze-drying the photosensitizer from a non-saline solution and reconstituting the freeze-dried product with a non-saline diluent. The present invention provides a process of preparing freeze-dried PHE which is quickly accomplished because of its small initial volume, avoids precipitation of the PHE component, and which results in a product that is homogeneous in nature.

A description of the PHE active ingredient of the present invention and methods for preparing it are described in the aforementioned U.S. Pat. No. 4,649,151.

In accordance with the present invention, the freeze-dried PHE preparation is manufactured from a concentrate containing approximately 15 mg/ml of PHE in water. This concentrate then undergoes the freeze-drying process and the resulting product is suitable for storage and shipping. The freeze-dried product is reconstituted prior to use with sufficient non-saline diluent such as 5% Dextrose Injection to provide an isotonic 2.5 mg/ml solution for use in treatment or diagnosis of a patient.

In a preferred embodiment of the present invention, approximately 5 ml of the approximately 15 mg/ml PHE concentrate is placed in a vial suitable for freeze-drying. Thus, each vial carries a label claim of 75 mg polyhematoporphyrin ethers/esters per vial. Each vial is then frozen in a freeze-drying chamber to a product temperature of $-35°$ C. or less for sufficient time to completely freeze the product. It is then freeze-dried at an elevated shelf temperature until a product with a satisfactory moisture content is obtained, whereupon the chamber is returned to atmospheric pressure and the vials are then sealed. Because of the small initial fill volume (5 ml), the product is quickly freeze-dried, usually within a 24 hour period. This greatly reduces the cost compared with freeze-drying large volumes of more dilute solution. The resulting product may then be stored at room temperature for over 6 months without appreciable loss of potency. Prior to administration to a patient, the freeze-dried product is reconstituted with 30 ml of 5% Dextrose Injection, providing an isotonic 2.5 mg/ml solution.

The diluent used for reconstitution of the freeze-dried product is preferably 5% Dextrose Injection, but other non-saline diluents such as Sterile Water for Injection may be used.

When the freeze-dried product is reconstituted with normal saline and filtered using 0.2 $\mu$m filters, large numbers of undesirable particles may be observed under an optical microscope. No significant particulate formation is observed when the product is reconstituted with Dextrose Injection. Therefore, it is desirable that a non-saline diluent be used.

It is contemplated that other ingredients may be included in the formulation of the product of the present invention. These may include buffers to affect the pH of the solution, wetting or emulsifying agents, antimicrobial agents and/or preservatives, as necessary. Also, non-electrolyte bulking agents such as mannitol or dextrose may be included to improve the characteristics of the freeze-dried cake. Many variations of the above, along with other suitable vehicles will suggest themselves to those skilled in the art in light of the foregoing detailed description. All such obvious variations are contemplated to be within the scope of the appended claims.

The following examples display a comparison of the freeze-dried preparation to the presently available frozen solution. The examples are not to be construed as limiting the scope of the invention set forth in the claims.

EXAMPLE 1

A concentrated PHE aqueous solution containing approximately 15 mg/ml polyhematoporphyrin ethers/esters is prepared in accordance with the procedures outlined by Dougherty in U.S. Pat. No. 4,649,151. The concentrate is stored frozen and thawed prior to freeze-drying in a 3° C. (±2° C.) cold water bath or under refridgeration at 2°–8° C. to allow gradual thawing. The thawed concentrate is then weighed and poured into a tared glass mixing vessel which has been protected from light. The batch is then mixed until homogeneous.

Once a homogeneous mixture is obtained, the pH of the thawed bulk concentrate is measured and adjusted to pH 7.2–7.8 with 5% hydrochloric acid or 5% sodium hydroxide aqueous solution, if necessary. The concentrate is then sterile filtered using a two stage filtering process involving a 0.45 μm polyvinylidene difluoride prefilter followed by a 0.2 μm sterile filter of the same type.

After filtration of the concentrate is completed, an appropriate volume to yield a 75 mg label claim per vial is filled into 30 ml vials. The vials are then placed into the freeze-drying chamber. The sterile concentrate is frozen to a product temperature of −35° C. or less for at least 2 hours. It is then freeze-dried at a shelf temperature of +35° C. until the product temperature reaches +20° C. to +25° C. and held at that temperature for 5 hours. The chamber is then returned to atmospheric temperature by venting with anhydrous nitrogen and the vials are stoppered, removed from the chamber, and sealed.

Prior to use in photodynamic therapy with a patient, the vial contents are reconstituted with 30.0 ml of 5% Dextrose for Injection.

EXAMPLE 2

Freeze-dried PHE with a moisture content of less than 1% as measured in a Karl Fischer assay is prepared according to the procedure of Example 1, with the added step, after holding the product at a temperature of +20° C. to +25° C. for 5 hours, of raising the product temperature to +33° C. to +37° C. and holding the product at that temperature for 6–10 hours. The chamber is then returned to atmospheric pressure as in Example 1 and the vials are stoppered and sealed.

EXAMPLE 3

Freeze-dried PHE was prepared in accordance with the procedure of Example 1. The product was then tested for stability at varying temperatures and time intervals by high pressure liquid chromatography (HPLC) under the following conditions:
Mobile Phase A: 1:1:1 mixture of tetrahydrofuran, methanol, and water containing 0.02% glacial acetic acid pH adjusted to 5.0–5.1 with in NaOH.
Mobile Phase B: 90% tetrahydrofuran in water.
Column: Ultrasphere ODS, 5 micron particle size 150×4.6 mm (Beckman).
Temperature: Ambient
Flow Rate: 1.0 ml/minute
Injection Volume: 20 mcl
Detection Mode: UV absorbance at 410 nm
Solvent Program:
  100% mobile phase A until Protoporphyrin peak is completely eluted (about 9.5 to 13 minutes)
  Linear program to 100% mobile phase B for one minute
  100% mobile phase B until PHE is completely eluted (about 16 to 25 minutes)
  Linear program to 100% mobile phase A for three minutes
  Equilibrate with 100% mobile phase A for at least 5 minutes between injections.
The results are set forth in Table 1.

TABLE 1

| | PHE Freeze-Dried PHE Content, HPLC Area Percent | | | | |
|---|---|---|---|---|---|
| Conditions | Batch 1 | Batch 2 | Batch 3 | Batch 4 | Batch 5 |
| Initial | 100.00 | 100.00 | 100.00 | 100.00 | 100.00 |
| −20° C., 6 mo. | 95.2 | 95.6 | 98.7 | — | — |
| 3° C., 3 mo. | 95.2 | 95.6 | 100.9 | 101.0 | 100.2 |
| 3° C., 6 mo. | 93.9 | 92.8 | 98.0 | — | — |
| 23° C., 1 mo. | 95.2 | 93.7 | 98.9 | 96.5 | 96.6 |
| 23° C., 3 mo. | 93.4 | 93.3 | 93.5 | 94.7 | 94.7 |
| 23° C., 6 mo. | 93.0 | 93.7 | 93.0 | — | — |
| 37° C., 1 mo. | 93.2 | 92.7 | 93.6 | 93.4 | 92.6 |
| 37° C., 3 mo. | 90.1 | 89.9 | 89.7 | 92.4 | 91.4 |

HPLC stability testing data for the PHE frozen solution under similar conditions displayed the results set forth in Table 2:

TABLE 2

| | PHE Frozen Solution PHE Content, HPLC Area Percent | | |
|---|---|---|---|
| Conditions | Batch 1 | Batch 2 | Batch 3 |
| Initial | 100 | 100 | 100 |
| −20° C., 6 mo. | 92.9 | 101.3 | — |
| +5° C., 3 mo. | 83.2 | 93.4 | 85.2 |
| 5° C., 6 mo. | 81.4 | 86.9 | 84.1 |
| 5° C., 9 mo. | 77.1 | 81.9 | 77.9 |
| 25° C., 3 mo. | 82.4 | 91.2 | 83.8 |
| 25° C., 6 mo. | 86.4 | 93.9 | 87.8 |
| 25° C., 9 mo. | 77.1 | 91.5 | 88.8 |

An examination of the data set forth in Tables 1 and 2 shows that the freeze-dried PHE composition of the present invention shows greater and more consistent stability than the frozen solution, and maintains its potency for at least 6 months at room temperature.

EXAMPLE 4

PHE freeze-dried was prepared in accordance with Example 1 and tested for particulates using a HIAC counter. The following results were obtained:

TABLE 3

| | PHE Freeze-Dried Particulate Analysis* Number of Particles per Container (30 ml) | | | | |
|---|---|---|---|---|---|
| | Stability Batch No. | | | | |
| Conditions | Batch 1 | Batch 2 | Batch 3 | Batch 4 | Batch 5 |
| Initial | — | — | — | 200 | 300 |
| 3° C., 3 mo. | — | — | — | 400 | 300 |
| 3° C., 6 mo. | 4600 | 1400 | 500 | — | — |
| 23° C., 3 mo. | — | — | — | 400 | 400 |
| 23° C., 6 mo. | 5700 | 1500 | 600 | — | — |

All numbers represent particles ≧10μ in size.
*Measurements performed with a HIAC Instrument.

Particulate analysis of the frozen solution using a Coulter counter is set forth in Table 4.

TABLE 4

| | PHE Frozen Solution Particulate Analysis* Number of Particles per Container (30 ml) | | |
|---|---|---|---|
| | Stability Batch No. | | |
| Conditions | Batch 1 | Batch 2 | Batch 3 |
| Initial | — | 1163 | — |
| −20° C., 6 mo. | 2039 | 4184 | 605 |

TABLE 4-continued

PHE Frozen Solution
Particulate Analysis*
Number of Particles per Container (30 ml)

| | Stability Batch No. | | |
|---|---|---|---|
| Conditions | Batch 1 | Batch 2 | Batch 3 |
| +5° C., 3 mo. | 6372 | 16664 | 4555 |
| 5° C., 6 mo. | 9565 | 28768 | 7160 |
| 5° C., 9 mo. | 19406 | 42730 | 21104 |
| 25° C., 3 mo. | 14059 | 18457 | 10519 |
| 25° C., 6 mo. | 10211 | 5332 | 9742 |
| 25° C., 9 mo. | 32197 | 14338 | 23501 |

*Measurements performed with a Coulter Counter.

An examination of the above data shows that the freeze-dried product maintains a level of particle formation well below the USP specification for injectables of not more than 10,000 particles greater than or equal to 10 micrometers per container whereas the frozen solution shows significant particle formation at temperatures above −20° C. at intervals as low as 3 months.

EXAMPLE 5

The freeze-dried PHE prepared in accordance with Example 1 was tested for biological activity using a procedure disclosed by T. Dougherty, et al., J. Nat. Cancer Inst. 55:115. In accordance with that procedure SMT-F tumors from "donor" DBA/2HA mice were implanted onto DBA/2HA mice for testing. Following implantation, ten mice with tumor dimensions 4 mm×4 mm to 6 mm×6 mm were chosen and injected intraperitoneally with 4.2 mg/kg of PHE solution prepared by reconstituting the freeze-dried PHE with 5% Dextrose in water. Twenty four hours following dosing, the tumors were irradiated for thirty minutes with a xenon arc lamp using 630 nm red light at a distance that corresponds to a light intensity of 157.5 mW/cm$^2$, as read on a power meter. Passing results are interpreted as no visible or palpable tumor in 50% or more of the ten test mice 7 days following irradiation. The results of the bioassay using the reconstituted freeze-dried PHE are set forth below in Table 5.

TABLE 5

PHE Freeze-Dried
Bioassay Data

| | Bioassay Results Stability Batch No. | | | | |
|---|---|---|---|---|---|
| | Batch 1 | Batch 2 | Batch 3 | Batch 4 | Batch 5 |
| Initial | Pass | Pass | Pass | Pass | Pass |
| −20° C., 6 mo. | Pass | Pass | — | — | — |
| 3° C., 3 mo. | Pass | Pass | — | Pass | Pass |
| 3° C., 6 mo. | Pass | Pass | Pass | — | — |
| 23° C., 1 mo. | Pass | Pass | Pass | Pass | Pass |
| 23° C., 3 mo. | Pass | Pass | — | Pass | Pass |
| 23° C., 6 mo. | Pass | Pass | Pass | — | — |
| 37° C., 1 mo. | Pass | Pass | Pass | Pass | Pass |
| 37° C., 3 mo. | Pass | Pass | — | Pass | Pass |

The results of a bioassay of the PHE frozen solution, using the same procedure as outlined above, are set forth in Table 6.

TABLE 6

PHE Frozen Solution
Particulate Analysis

| | Bioassay Results for Batches | | |
|---|---|---|---|
| Conditions | Batch 1 | Batch 2 | Batch 3 |
| Initial | Pass | Pass | — |
| −20° C., 3 mo. | — | — | Pass |
| −20° C., 6 mo. | Fail | Pass | — |
| −20° C., 9 mo. | Fail | Pass | Fail |
| 5° C., 3 mo. | Pass | Pass | Fail |
| 5° C., 6 mo. | Fail | Fail | Fail |
| 5° C., 9 mo. | Pass | Fail | Pass |
| 25° C., 3 mo. | Fail | Pass | Pass |
| 25° C., 6 mo. | Fail | Fail | Fail |
| 25° C., 9 mo. | Pass | Fail | Fail |

It can be seen by a comparison of the results contained in Tables 5 and 6, that the freeze-dried PHE of the present invention maintains its biological activity in in vivo tests at intervals of at least 6 months at room temperature, whereas the frozen solution shows considerable variability in biological activity under similar conditions.

EXAMPLE 6

Freeze-dried PHE containing mannitol as bulking agent is prepared in accordance with the procedure of Example 1 by adding an amount of mannitol equal to the weight of PHE to the thawed concentrate in the glass mixing vessel.

EXAMPLE 7

Freeze-dried PHE containing dextrose as a bulking agent is prepared as in Example 6, substituting dextrose for mannitol.

What is claimed is:
1. A pharmaceutical composition comprising a freeze-dried preparation of polyhematoporphyrin ether/esters wherein said freeze-dried preparation does not contain sodium chloride.
2. A pharmaceutical composition which consists essentially of the freeze-dried composition of claim 1 as active ingredient in association with a pharmaceutically acceptable excipient.
3. A pharmaceutical composition according to claim 2 in which the pharmaceutically acceptable excipient is a non-electrolyte bulking agent.
4. A pharmaceutical composition according to claim 3 in which the non-electrolyte bulking agent is mannitol or dextrose.
5. A freeze-dried pharmaceutical composition according to claim 1 containing less than 1% residual water.
6. A pharmaceutical composition comprising a freeze dried preparation according to claim 1 reconstituted with 5% dextrose for injection.

* * * * *